United States Patent
Lee et al.

(10) Patent No.: US 7,125,443 B2
(45) Date of Patent: Oct. 24, 2006

(54) LIGHTFAST COLORANT AND LIGHTFAST INK COMPOSITION INCLUDING THE SAME

(75) Inventors: Kyung-hoon Lee, Gyeonggi-do (KR); Seung-min Ryu, Gyeonggi-do (KR); Yeon-kyoung Jung, Seoul (KR)

(73) Assignee: Samsung Electronics Co., Ltd., Suwon (KR)

( * ) Notice: Subject to any disclaimer, the term of this patent is extended or adjusted under 35 U.S.C. 154(b) by 169 days.

(21) Appl. No.: 10/802,949

(22) Filed: Mar. 18, 2004

(65) Prior Publication Data

US 2004/0182279 A1 Sep. 23, 2004

(30) Foreign Application Priority Data

Mar. 21, 2003 (KR) .................... 10-2003-0017746

(51) Int. Cl.
*C09D 11/00* (2006.01)
*C09B 1/20* (2006.01)
*C09B 43/124* (2006.01)
*C09B 43/132* (2006.01)
*C09B 43/22* (2006.01)
*C09B 43/30* (2006.01)

(52) U.S. Cl. ............... 106/31.44; 106/31.5; 106/31.51; 106/31.52; 534/783; 534/812; 534/829; 534/865; 534/874; 552/212

(58) Field of Classification Search ............... 534/783, 534/812, 829, 865, 874; 552/212; 106/31.44, 106/31.5, 31.51, 31.52
See application file for complete search history.

(56) References Cited

U.S. PATENT DOCUMENTS 4,911,732 A * 3/1990 Neumann et al. ............... 8/442
5,075,429 A * 12/1991 Yamamoto et al. ......... 534/768

FOREIGN PATENT DOCUMENTS

| EP | 1 006 161 A1 | | 6/2000 |
| JP | 01-97689 | * | 4/1989 |
| JP | 05-255604 | * | 10/1993 |

* cited by examiner

*Primary Examiner*—Fiona T. Powers
(74) *Attorney, Agent, or Firm*—Staas & Halsey LLP

(57) ABSTRACT

A lightfast colorant and a lightfast ink composition include a lightfast colorant that is derived by covalently binding a benzophenone derivative and a conventional colorant and that imparts effective lightfastness and long-term storage stability to an ink composition that is prepared with the same.

15 Claims, No Drawings

LIGHTFAST COLORANT AND LIGHTFAST INK COMPOSITION INCLUDING THE SAME

CROSS-REFERENCE TO RELATED APPLICATIONS

This application claims the priority of Korean Patent Application No. 2003-17746, filed on Mar. 21, 2003, in the Korean Intellectual Property Office, the disclosure of which is incorporated herein in its entirety by reference.

BACKGROUND OF THE INVENTION

1. Field of the Invention

The present invention relates to a lightfast colorant and a lightfast ink composition including the same, and more particularly, to a lightfast colorant that is derived by chemically binding a benzophenone derivative to the molecular structure of a conventional colorant, and a lightfast ink composition containing the same.

2. Description of the Related Art

Ink-jet printing, which is a kind of non-impact printing, has the advantages of low noise generation, compared to impact printing, and easy color printing realization, compared to laser beam printing.

There are two types of non-impact printing: continuous ink-jet printing and drop-on-demand (DOD) printing. In continuous ink-jet printing, while ink is continuously discharged, a change in an electromagnetic field is induced to control a direction in which the ink is jetted. DOD printing, in which micro droplets of ink are jetted, includes thermal-bubble ink-jet printing and piezoelectric ink-jet printing. In thermal-bubble ink-jet printing, ink is discharged by a pressure generated by the swelling of bubbles that are generated as the ink is heated. In piezoelectric ink-jet printing, ink is discharged by a pressure generated by using a piezoelectric plate that may be mechanically deformable by electricity.

Recently, a dot-size of ink-jet printers utilized has become smaller, and there has been an increasing need for high-resolution, high-quality prints. Smaller dot-size ink-jet printers require a head having smaller nozzle orifices. However, smaller nozzle orifices are susceptible to being clogged by precipitates, and thus affect the size of ink droplets and the performance of the printer. It is obvious that the composition of the ink affects the clogging of the nozzle orifices. For this reason, a wetting agent is commonly added to the ink-jet ink compositions.

An ink composition for ink-jet printing contains a colorant, a solvent, and an additive. A dye or a pigment may be used as the colorant. However, using a dye as the colorant is limited because it causes a print to have poor lightfast and water-fast properties. When using a pigment as the colorant, a resulting print is more lightfast and water-fast than a print prepared using a dye, but is still susceptible to color change or discoloration when exposed to ultraviolet (UV) light. An additional lightfastness enhancer may be used. However, negative side effects, for example, the clogging of the nozzle orifices by agglomerated ink, the formation of a heterogeneous ink composition, and the like, occur when the lightfastness enhancer is used.

As an example, EP 1006161 A1 discloses an ink composition in which a colorant covered with a polymer that includes UV-absorbing and/or lightfast sites is dispersed. The ink composition that includes such a colorant coated with a UV-absorbing polymer is unstable due to poor dispersion stability of the polymer-coated colorant particles and the weak binding force between the colorant and the polymer.

SUMMARY OF THE INVENTION

The present invention provides a lightfast colorant that minimizes the above-listed and/or other problems.

The present invention provides a lightfast ink composition that contains the lightfast colorant.

In one aspect of the present invention, a lightfast colorant comprises a benzophenone derivative of formula (1) below:

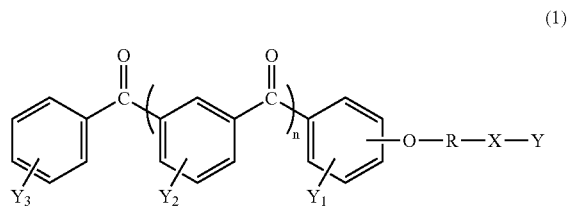

(1)

wherein $Y_1$ is one selected from the group consisting of —H, —OH, —NH$_2$, —NHR$_1$, —N(R$_1$)$_2$, —SH, and a C$_1$–C$_{30}$ heteroalkyl group, where R$_1$ is a C$_1$–C$_6$ alkyl group; each of $Y_2$ and $Y_3$, which may be the same or different, is independently selected from the group consisting of —H, —OH, —NH$_2$, —NHR$_1$, —N(R$_1$)$_2$, where R$_1$ is a C$_1$–C$_6$ alkyl group, —SH, a substituted or unsubstituted C$_1$–C$_{30}$ alkyl group, a substituted or unsubstituted C$_1$–C$_{30}$ alkenyl group, a substituted or unsubstituted C$_1$–C$_{30}$ alkynyl group, a substituted or unsubstituted C$_1$–C$_{30}$ heteroalkyl group, a substituted or unsubstituted C$_6$–C$_{30}$ aryl group, a substituted or unsubstituted C$_7$–C$_{30}$ arylalkyl group, a substituted or unsubstituted C$_3$–C$_{30}$ heteroaryl group, and a substituted or unsubstituted C$_4$–C$_{30}$ heteroarylalkyl group; n is an integer from 0 to 6; R is selected from the group consisting of a substituted or unsubstituted C$_1$–C$_{30}$ alkylene group, a substituted or unsubstituted C$_1$–C$_{30}$ alkenylene group, a substituted or unsubstituted C$_1$–C$_{30}$ alkynylene group, a substituted or unsubstituted C$_1$–C$_{30}$ heteroalkylene group, a substituted or unsubstituted C$_6$–C$_{30}$ arylene group, a substituted or unsubstituted C$_7$–C$_{30}$ arylenealkylene group, a substituted or unsubstituted C$_3$–C$_{30}$ heteroarylene group, and a substituted or unsubstituted C$_4$–C$_{30}$ heteroarylenealkylene group; X is a linker selected from the group consisting of —CONH—, —NHCO—, —COO—, —OCO—, —CO—, —O—, —S—, —SO$_2$—, —SO$_3$—, —O—P(=O)(OH)—O—, and —O—P(OH)—O—; and Y is a colorant residue.

The colorant residue Y is a remaining moiety of a colorant, which may be either a dye or a pigment, the moiety excluding the linker X that is an amide bond, an ester bond, a carbonyl bond, a sulfonyl bond, and the like, and links the colorant and a benzophenone derivative. The linker X is formed by a condensation reaction between a functional group in the molecular structure of the colorant (dye or pigment), such as a hydroxy group, an amino group, a sulfonic acid group, a phosphoric acid group, and the like, and a functional group of the benzophenone derivative, such as a hydroxy group, an amine group, a carboxyl group, and the like.

In another aspect of the present invention, a lightfast ink composition includes at least one of the lightfast colorants having formula (1) above and an aqueous medium.

Another lightfast ink composition, according to an embodiment of the present invention, includes a colorant, at least one of the lightfast colorants having formula (1) above, and an aqueous medium.

Additional aspects and/or advantages of the invention will be set forth in part in the description which follows and, in part, will be obvious from the description, or may be learned by practice of the invention.

DETAILED DESCRIPTION OF THE PREFERRED EMBODIMENTS

Embodiments of a lightfast colorant according to an embodiment of the present invention will be described in detail.

A lightfast colorant according to an embodiment of the present invention is derived by chemically binding a lightfast enhancer and a colorant. In other words, a lightfast colorant according to an embodiment of the present invention is obtained by chemically binding a conventional colorant and a benzophenone derivative. The lightfast colorant according to an embodiment of the present invention improves the long-term storage stability of an ink composition without requiring adding a separate lightfastness enhancer. Also, since water soluble functional groups, such as an amino group, a hydroxy group, a carboxyl group, a sulfonic acid group, a phosphoric acid group, and the like, are converted into an amide group, an ester group, a carbonyl group, or a sulfonyl group, the water-fastness of a resulting print is also improved.

A lightfast colorant according to an embodiment of the present invention is a benzophenone derivative of formula (1) below:

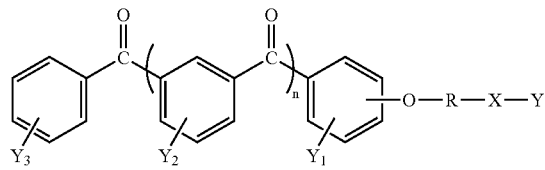

(1)

In formula (1) above, $Y_1$ is one selected from the group consisting of —H, —OH, —NH$_2$, —NHR$_1$, —N(R$_1$)$_2$, —SH, and a C$_1$–C$_{30}$ heteroalkyl group, where R$_1$ is a C$_1$–C$_6$ alkyl group; each of $Y_2$ and $Y_3$, which may be the same, is independently selected from the group consisting of —H, —OH, —NH$_2$, —NHR$_1$, —N(R$_1$)$_2$, where R$_1$ is a C$_1$–C$_6$ alkyl group, —SH, a substituted or unsubstituted C$_1$–C$_{30}$ alkyl group, a substituted or unsubstituted C$_1$–C$_{30}$ alkenyl group, a substituted or unsubstituted C$_1$–C$_{30}$ alkynyl group, a substituted or unsubstituted C$_1$–C$_{30}$ heteroalkyl group, a substituted or unsubstituted C$_6$–C$_{30}$ aryl group, a substituted or unsubstituted C$_7$–C$_{30}$ arylalkyl group, a substituted or unsubstituted C$_3$–C$_{30}$ heteroaryl group, and a substituted or unsubstituted C$_4$–C$_{30}$ heteroarylalkyl group; n is an integer from 0 to 6; R is selected from the group consisting of a substituted or unsubstituted C$_1$–C$_{30}$ alkylene group, a substituted or unsubstituted C$_1$–C$_{30}$ alkenylene group, a substituted or unsubstituted C$_1$–C$_{30}$ alkynylene group, a substituted or unsubstituted C$_1$–C$_{30}$ heteroalkylene group, a substituted or unsubstituted C$_6$–C$_{30}$ arylene group, a substituted or unsubstituted C$_7$–C$_{30}$ arylenealkylene group, a substituted or unsubstituted C$_3$–C$_{30}$ heteroarylene group, and a substituted or unsubstituted C$_4$–C$_{30}$ heteroarylenealkylene group; X is a linker selected from the group consisting of —CONH—, —NHCO—, —COO—, —OCO—, —CO—, —O—, —S—, —SO$_2$—, —SO$_3$—, —O—P(=O)(OH)—O—, and —O—P(OH)—O—; and Y is a colorant residue.

The colorant residue Y refers to a remaining moiety of the colorant, which may be either a dye or a pigment, the moiety excluding the linker X that is an amide bond, an ester bond, a carbonyl bond, a sulfonyl bond, and the like, and links the colorant and a benzophenone derivative.

The linker X is formed by a condensation reaction between a functional group in the molecular structure of the colorant (dye or pigment), such as a hydroxy group, an amino group, a sulfonic acid group, a phosphoric acid group, and the like, and a functional group of the benzophenone derivative, such as a hydroxy group, an amine group, a carboxyl group, and the like.

The lightfast colorant according to an embodiment of the present invention is derived by chemically binding a colorant having a functional group as described above and a benzophenone derivative that imparts lightfastness. In other words, the lightfast colorant of formula (1) according to an embodiment of the present invention may be obtained by covalently binding a colorant and a benzophenone derivative of formula (2) below through a chemical bond, such as an amide bond, an ester bond, a carbonyl bond, a sulfonyl bond, and the like.

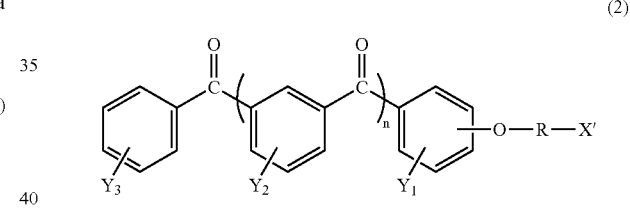

(2)

In formula (2) above, $Y_1$, $Y_2$, $Y_3$, n, and R are the same as in formula (1) above; and X' is a reactive functional group selected from the group consisting of a carboxyl group, a hydroxy group, an amino group, a sulfonic acid group, and a phosphoric acid group.

As illustrated in the following reaction schemes (1) through (4), the lightfast colorant of formula (1) according to an embodiment of the present invention is derived by a condensation reaction of a carboxyl group, a hydroxy group, an amino group, a sulfonic acid group, a phosphoric acid group, and the like, which are present in the molecular structure of a source colorant and the reactive functional group X' of the benzophenone derivative of formula (2).

Reaction scheme (1)

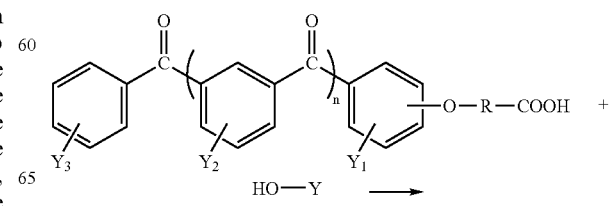

-continued

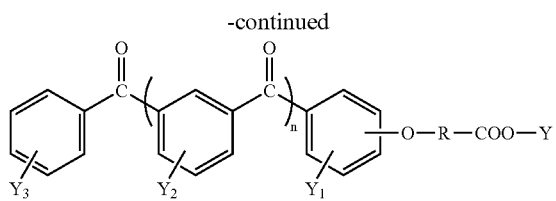

Reaction scheme (2)

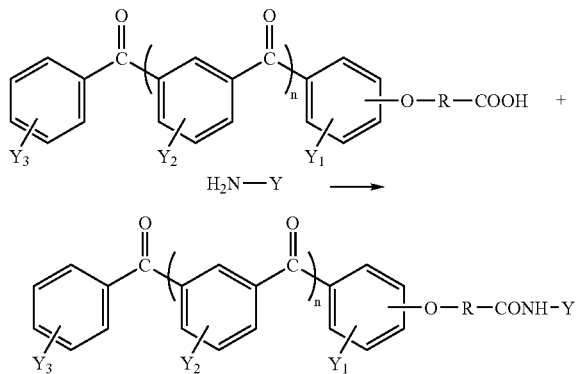

Reaction scheme (3)

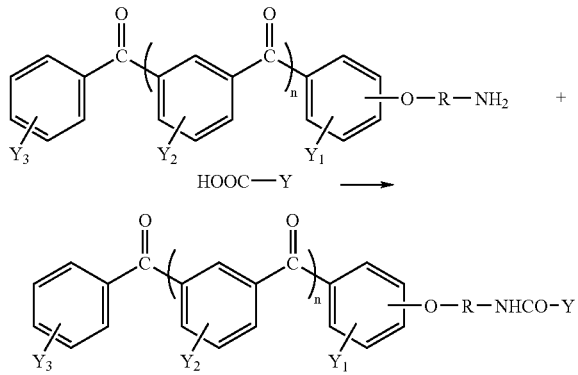

Reaction scheme (4)

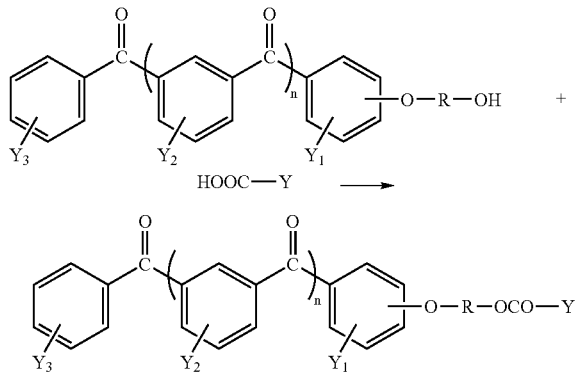

In Reaction schemes (1) through (4) above, $Y_1$, $Y_2$, $Y_3$, n, and R are the same as in formula (1).

The colorant that is chemically bound with the benzophenone derivative of formula (2) is expressed as HO—Y, $H_2N$—Y, and HOOC—Y, where Y refers to the above-described colorant residue, in the reaction schemes (1) through (4) and may be any dye or pigment that is commonly used in ink compositions provided that it includes an amino group, a carboxyl group, a hydroxyl group, a phosphoric acid group, a sulfonic acid group, and the like, which may react with the reactive functional group X' of the benzophenone derivative of formula (2) in the molecular structure thereof. Specific examples of a dye include, but are not limited to, C.I DIRECT BLACK NOS. 9, 17, 19, 22, 32, 51, 56, 91, 94, 97, 166, 168, 173, and 199; C.I DIRECT BLUE NOS. 1, 10, 15, 22, 77, 78, 80, 200, 201, 202, 203, 207, and 211; C.I DIRECT RED NOS. 2, 4, 9, 23, 31, 39, 63, 72, 83, 84, 89, 111, 173, 177, 184, and 240; C.I DIRECT YELLOW NOS. 8, 9, 11, 12, 27, 28, 29, 33, 35, 39, 41, 44, 50, 53, and 58; and other direct dyes, disperse dyes, basic dyes, acid dyes, azo dyes, and the like. Specific examples of a pigment for the colorant include, but are not limited to, carbon black, graphite, vitreous carbon, activated charcoal, activated carbon, anthraquinones, phthalocyanine blue, phthalocyanine green, diazos, monoazos, pyranthrones, perylenes, quinacridones, and indigoid pigments.

As described above, in formulas (1) and (2), $Y_1$ is one selected from the group consisting of —H, —OH, —$NH_2$, —$NHR_1$, —$N(R_1)_2$, —SH, and a $C_1$–$C_{30}$ heteroalkyl group, where $R_1$ is a straight or branched $C_1$–$C_6$ alkyl group.

The heteroallyl group for $Y_1$ is a straight or branched heteroalkyl group having 1 to 30 carbon atoms, preferably, 1 to 20 carbon atoms, more preferably, 1 to 10 carbon atoms. The $C_{10}$–$C_{30}$ heteroalkyl group for $Y_1$ is a $C_1$–$C_{30}$ alkyl group including 1 to 3 hetero atoms selected from the group consisting of N, O, P, and S. Specific examples of such a heteroalkyl group include, but are not limited to, an oxymethyl group, an oxyethyl group, an oxypropyl group, a mercaptomethyl group, a mercaptoethyl group, a mercaptopropyl group, and the like. At least one hydrogen atom in the heteroalkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

As described above, $Y_2$ and $Y_3$ in formulas (1) and (2), which may be the same or different, are independently selected from the group consisting of —H, —OH, —$NH_2$, —$NHR_1$, —$N(R_1)_2$, where $R_1$ is a straight or branched $C_1$–$C_6$alkyl group, —SH, a substituted or unsubstituted $C_1$–$C_{30}$ alkyl group, a substituted or unsubstituted $C_1$–$C_{30}$alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group.

The alkyl group for $Y_2$ or $Y_3$ may be a straight or branched alkyl group having 1 to 30 carbon atoms, preferably, 1 to 20 carbon atoms, more preferably, 1 to 10 carbon atoms. Specific examples of such an alkyl group include, but are not limited to, a methyl group, an ethyl group, an n-propyl group, an isopropyl group, an n-butyl group, an isobutyl group, a sec-butyl group, a t-butyl group, a pentyl group, an iso-amyl group, a hexyl group, a heptyl group, an octyl group, a nonyl group, a decyl group, a dodecyl group, and the like, wherein at least one hydrogen atom in the alkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The alkenyl group for $Y_2$ or $Y_3$ may be a straight or branched alkenyl group having 1 to 30 carbon atoms, preferably, 1 to 20 carbon atoms, more preferably, 1 to 10 carbon atoms. The alkenyl group refers to an alkyl group that includes at least one carbon-carbon double bond in its molecular structure. Specific examples of such an alkenyl group include, but are not limited to, an ethylene group, a propylene group, a butylene group, a hexylene group, an allyl group, and the like. At least one hydrogen atom of the alkenyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The alkynyl group for $Y_2$ or $Y_3$ may be a straight or branched alkynyl group having 1 to 30 carbon atoms, preferably, 1 to 20 carbon atoms, more preferably, 1 to 10 carbon atoms. The alkynyl group refers to an alkyl group that includes at least one carbon-carbon triple bond in its molecular structure. Specific examples of such an alkynyl group include, but are not limited to, an acetylenyl group, a propylenyl group, and the like. At least one hydrogen atom of the alkynyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The heteroalkyl group for $Y_2$ or $Y_3$ may be a straight or branched heteroalkyl group having 1 to 30 carbon atoms, preferably, 1 to 20 carbon atoms, more preferably, 1 to 10 carbon atoms. The $C_{10}$–$C_{30}$ heteroalkyl group for each of $Y_2$ and $Y_3$ is a $C_1$–$C_{30}$ alkyl group including 1 to 3 hetero atoms selected from the group consisting of N, O, P, and S. Specific examples of such a heteroalkyl group include, but are not limited to, an oxymethyl group, an oxyethyl group, an oxypropyl group, a mercaptomethyl group, a mercaptoethyl group, a mercaptopropyl group, and the like. At least one hydrogen atom in the heteroalkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The aryl group for $Y_2$ or $Y_3$ may be an aryl group having 6 to 30 carbon atoms, preferably, 6–18 carbon atoms, and more preferably, 6 to 12 carbon atoms, the aryl group being a hydrocarbon group that includes at least one aromatic ring. Specific examples of such an aryl group include, but are not limited to, aromatic radicals, such as phenyl, naphthyl, biphenyl, tetrahydronaphthyl, indanyl, and the like, with phenyl and naphthyl being preferred. At least one hydrogen atom in the aryl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The substituted or unsubstituted arylalkyl group for each of $Y_2$ and $Y_3$ may have 7 to 30 carbon atoms, preferably, 7 to 19 carbon atoms, more preferably, 7 to 13 carbon atoms. Specific examples of such an arylalkyl group include, but are not limited to, benzyl, phenetyl, triphenylmethyl, diphenylmethyl, phenylbutyl, neophyl, and the like. At least one hydrogen atom in the arylalkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like. The arylalkyl group for each of $Y_2$ and $Y_3$ may include a carbon-carbon double bond or carbon-carbon triple bond in its alkyl residue, like a styryl group.

The substituted or unsubstituted heteroaryl group for each of $Y_2$ and $Y_3$ may have 3 to 30 carbon atoms, preferably, 3 to 18 carbon atoms, more preferably, 3 to 12 carbon atoms. The heteroaryl group refers to an aromatic carbocyclic system that contains one, two, or three hetero atoms selected from the group consisting of N, O, P, and S, wherein at least one of the hetero atoms may be oxidized or quaternarized into, an N-oxide or a quaternary salt. Examples of such a heteroaryl group include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, an N-oxide of the foregoing groups, such as pyridyl N-oxide and quinolinyl N-oxide, and a quaternary salt of the foregoing materials, and the like. At least one hydrogen atom in the heteroaryl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The substituted or unsubstituted heteroarylalkyl group for each of $Y_2$ and $Y_3$ may have 4 to 30 carbon atoms, preferably, 4 to 18 carbon atoms, more preferably, 4 to 12 carbon atoms. The heteroarylalkyl group refers to a heteroaryl group that has an alkyl group substituted for some hydrogen atom. Examples of such a heteroarylalkyl group include, but are not limited to, thienylmethyl, thienylethyl, benzothienylmethyl, benzothienylethyl, pyridylmethyl, pyridylethyl, pyridylpropyl, pyrazinylmethyl, pyrazinylethyl, pyrimidinylmethyl, pyrimidinylethyl, pyridazinylmethyl, pyridazinylethyl, quinolinylmethyl, quinolinylethyl, quinoxalinylmethyl, quinoxalinylethyl, imidazolylmethyl, imidazolylethyl, furanylmethyl, furanylethyl, and the like. At least one hydrogen atom in the heteroarylalkyl group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

In formula (1) and (2) above, R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted heteroarylene group, and a substituted or unsubstituted $C_4$–$C_{30}$ heteroarylenealkylene group. The alkylene group, alkenylene group, alkynylene group, heteroalkylene group, arylene group, arylenealkylene (or alkylenearylene) group, heteroarylene group, and heteroarylenealkylene (or heteroalkylenearylene) group are divalent radicals that may be incorporated in the middle of compounds and which correspond to an alkyl group, alkenyl group, alkynyl group, heteroalkyl group, aryl group, arylalkyl group, heteroaryl group, and heteroarylalkyl group, respectively, which are monovalent radicals positioned at an end of compounds.

The alkylene group for R may be a straight or branched radical having 1 to 30 carbon atoms, preferably, 1 to 20 carbon atoms, more preferably, 1 to 10 carbon atoms. Specific examples of such an alkylene group include, but are not limited to, a methylene group, an ethylene group, a n-propylene group, an isopropylene group, a n-butylene group, an isobutylene group, a sec-butylene group, a t-butylene group, a n-pentylene group, a sec-pentylene group, a t-pentylene group, a hexylene group, a heptylene group, an octylene group, a nonylene group, a decylene group, a dodecylene group, and the like. At least one hydrogen atom in the alkylene group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The alkenylene group or alkynylene group for R may have 1 to 30 carbon atoms, preferably, 1 to 20 carbon atoms, more preferably, 1 to 10 carbon atoms. The $C_1$–$C_{30}$ alkenylene group and $C_1$–$C_{30}$ alkynylene group correspond to the $C_1$–$C_{30}$ alkylene groups, the only difference being that they have at least one carbon-carbon double bond or carbon-carbon triple bond, respectively. At least one hydrogen atom in the alkenylene or alkynylene group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The heteroalkylene group for R may have 1 to 30 carbon atoms, preferably, 1 to 20 carbon atoms, more preferably, 1 to 10 carbon atoms. The heteroalkylene group refers to an alkylene group that includes one, two, or three hetero atoms selected from the group consisting of N, O, P, and S. Specific examples of such a heteroalkylene group include an oxymethylene group, an oxyethylene group, a propoxy group, a mercaptomethylene group, a mercaptoethylene group, a mercaptopropoxy group, and the like. At least one hydrogen atom in the heteroalkylene group may be substituted with a halogen atom, a haloalkyl group, an alkoxyl group, a hydroxyl group, a nitro group, a cyano group, an amino group, a lower alkyl amino group, an amidino group, hydrazine, hydrazone, a carboxyl group or a salt thereof, a sulfonic acid group or a salt thereof, a phosphoric acid group or a salt thereof, and the like.

The arylene group for R may have 6 to 30 carbon atoms, preferably, 6 to 18 carbon atoms, more preferably, 1 to 12 carbon atoms. Specific examples of such an arylene group include, but are not limited to, aromatic groups, such as a phenylene group, a naphthylene group, a biphenylene group, a tetrahydronaphthylene group, an indanylene group, and the like, with the biphenylene group, biphenylene group, and nathphylene group being preferred. At least one hydrogen atom in the arylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

The arylenealkylene group for R may have 7 to 30 carbon atoms, preferably, 7 to 19 carbon atoms, more preferably, 7 to 13 carbon atoms. The arylenealkylene group refers to a divalent radical corresponding to an arylalkyl group and comprises an alkylenearylene group. Specific examples of such an arylenealkylene group include, but are not limited to, a methylenephenylene group, an ethylenephenylene group, a methylenenaphthylene group, an ethylenenaphthylene group, a methylenebiphenylene group, an ethylenebiphenylene group, an n-propylenephenylene group, an isopropylenephenylene group, and the like. At least one hydrogen atom in the arylenealkylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

The heteroarylene group for R may have 3 to 30 carbon atoms, preferably, 3 to 18 carbon atoms, more preferably, 3 to 12 carbon atoms. The heteroarylene group refers to a divalent aromatic, carbocyclic system containing one, two, or three hetero atoms as an aromatic ring backbone atom selected from the group consisting of N, O, P, and S. The heteroarylene group includes a divalent arylene group that has a hetero atom oxidized or quaternarized into, for example, an N-oxide or a quaternary salt. Specific examples of such a heteroarylene group include, but are not limited to, thienylene, benzothienylene, pyridylene, pyrazinylene, pyrimidinylene, pyridazinylene, quinolinylene, quinoxalinylene, imidazolylene, furanylene, benzofuranylene, thiazolylene, isoxazolylene, benzisoxazolylene, benzimidazolylene, triazolylene, pyrazolylene, pyrrolylene, indolylene, 2-pyridonylene, 4-pyridonylene, N-alkyl-2-pyrinonylene, pyrazinonylene, pyridazinonylene, pyrimidinonylene, oxazolonylene, an N-oxide of the foregoing groups, such as pyridylene N-oxide and quinolinylene N-oxide, and a quaternary salt of the foregoing groups. At least one hydrogen atom in the heteroarylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

The heteroarylenealkylene group for R may have 4 to 30 carbon atoms, preferably, 4 to 18 carbon atoms, more preferably, 4 to 12 carbon atoms. The heteroarylenealkylene group refers to a heteroarylene group that has alkylene groups substituted for some hydrogen atoms. Specific examples of such a heteroarylenealkylene group include, but are not limited to, thienylene methylene, thienylene ethylene, benzothienylene methylene, benzothienylene ethylene, pyridylene methylene, pyridylene ethylene, pyrazinylene methylene, pyrazinylene ethylene, pyrimidinylene methylene, pyrimidinylene ethylene, pyridazinylene methylene, pyridazinylene ethylene, quinolinylene methylene, quinolinylene ethylene, quinoxalinylene methylene, quinoxalinylene ethylene, imidazolylene methylene, imidazolylene ethylene, furanylene methylene, furanylene ethylene, and the like. At least one hydrogen atom in the heteroarylene-alkylene group may be substituted with a halogen atom, a haloalkyl group, an alkoxyl group, a hydroxyl group, a nitro group, a cyano group, an amino group, a lower alkylamino group, an amidino group, hydrazine, hydrazone, a carboxyl group or a salt thereof, a sulfonic acid group or a salt thereof, a phosphoric acid group or a salt thereof, and the like.

Specific examples of the lightfast colorant of formula (1) above include lightfast colorants having formulas (3) through (8) below.

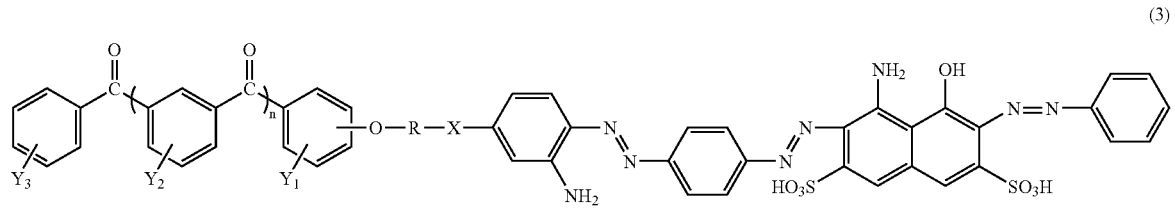

(3)

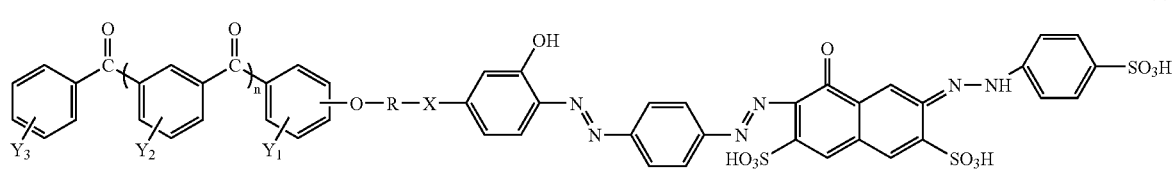

(4)

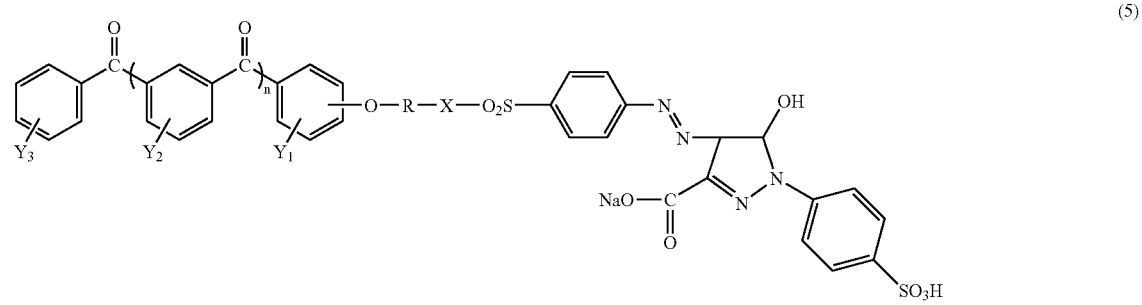

(5)

(6)

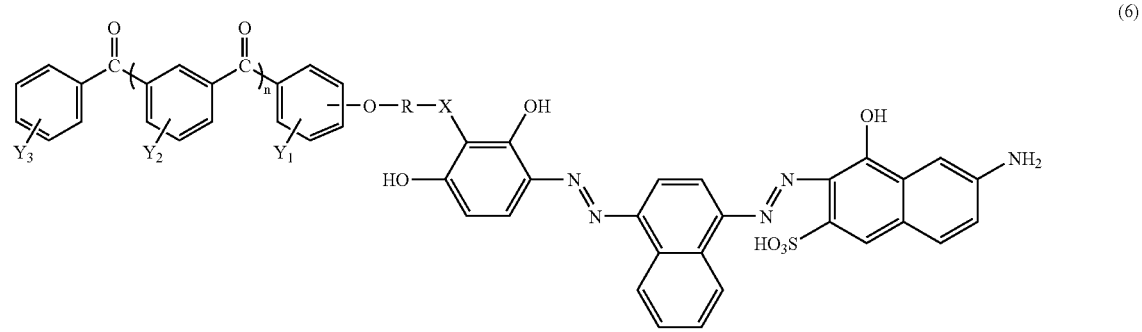

(7)

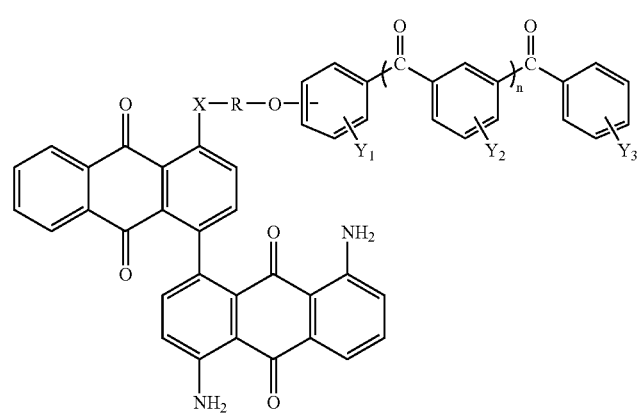

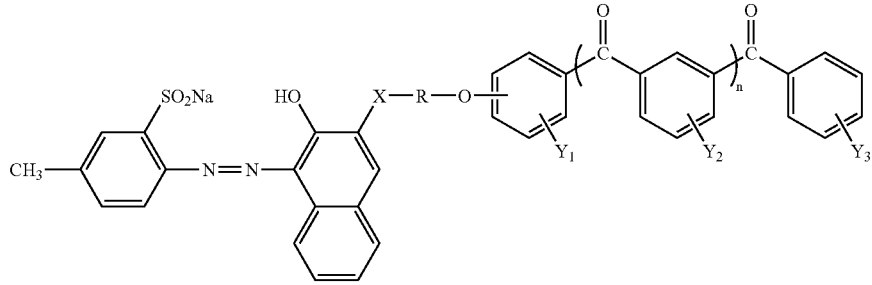

(8)

In formulas (3) through (8) above, $Y_1$, $Y_2$, $Y_3$, R, n, and X are the same as in formula (1) above.

Hereinafter, a lightfast ink composition that includes the above-described lightfast colorant of formula (1) according to an embodiment of the present invention will be described in detail.

An ink composition according to an embodiment of the present invention includes only the above lightfast colorant as a colorant component and does not include an additional conventional colorant. An ink composition according to an embodiment of the present invention includes at least one of the above-listed lightfast colorants, which have formula (1), and an aqueous medium. This ink composition may include 0.1–20 parts by weight, preferably, 1–10 parts by weight, of the lightfast colorant with respect to 100 parts by weight of the ink composition.

An ink composition according to another embodiment of the present invention includes both a conventional colorant and the lightfast colorant according to an embodiment of the present invention. In particular, the ink composition includes a conventional colorant, at least one of the above-listed lightfast colorants according to an embodiment of the present invention, which have formula (1), and an aqueous medium. This ink composition may include 1–25 parts by weight of the conventional colorant and 0.1–20 parts by weight of at least one of the lightfast colorants according to an embodiment of the present invention. A total amount of the conventional colorant and the lightfast colorant according to an embodiment of the present invention may be in the range of 1.1–45 parts by weight, preferably, 2–20 parts by weight, with respect to 100 parts by weight of the ink composition.

The ink compositions in the above embodiments of the present invention, including the conventional colorant and the lightfast colorant according to an embodiment of the present invention, are dissolved or dispersed in an aqueous medium.

The aqueous medium may be water alone, or a mixture of 5–50% by weight of an organic solvent and 50–95% by weight of water. The amounts of water and the organic solvent in the aqueous medium may be varied depending on various factors, for example, desired characteristics, such as the viscosity, surface tension, drying speed, and the like, of the ink composition. Desirable characteristics of ink compositions depend on printing methods of printers and types of printing media.

Examples of an organic solvent that may be used for the aqueous medium include, but are not limited to, alcohols, such as methyl alcohol, ethyl alcohol, n-propyl alcohol, isopropyl alcohol, n-butyl alcohol, sec-butyl alcohol, t-butyl alcohol, isobutyl alcohol, and the like; ketones, such as acetone, methylethyl ketone, diethyl ketone, diacetone alcohol, and the like; esters, such as methyl acetate, ethyl acetate, ethyl lactate, and the like; polyhydric alcohols, such as ethylene glycol, diethylene glycol, triethylene glycol, propylene glycol, butylene glycol, 1,4-butane diol, 1,2,4-butane triol, 1,5-pentanediol, 1,2,6-hexane triol, hexylene glycol, glycerol, glycerol ethoxylate, trimethylolpropane ethoxylate, and the like; ethers, such as ethylene glycol monomethyl ether, ethylene glycol monoethyl ether, diethylene glycol methyl ether, diethylene glycol ethyl ether, triethylene glycol monomethyl ether, triethylene glycol monoethyl ether, and the like; nitrogen-containing compounds, such as 2-pyrrolidone, N-methyl-2-pyrrolidone, and the like; and sulfur-containing compounds, such as dimethyl sulfoxide, tetramethylene sulfone, and thioglycol.

Each of the ink compositions according to the above embodiments of the present invention may further include at least one additive selected from the group consisting of a dispersant, a viscosity adjuster, a surfactant, a storage stabilizer, and a wetting agent.

When a pigment or a water-insoluble dye is used as the colorant, at least one dispersant may be added to the ink composition to improve the dispersion stability of the colorant. Any dispersants, including simpler structure, lower molecular weight dispersants, and larger molecular weight dispersants, such as block copolymers, which are not detrimental to physical properties, such as stability, and functionality of the ink composition, may be used without limitation.

Specific examples of lower molecular weight, simpler structure dispersants include, but are not limited to, polyvinyl alcohol (PVA), cellulosics, ethylene oxide modified phenols, an ethylene oxide/propylene oxide polymer, a sodium polyacrylate solution (TEGO, DISPERSE 715W), a modified polyacryl resin solution (TEGO, DISPERSE 735W), a solution of alkylol ammonium salt of a low molecular weight carboxylic polymer (BYK-CHEMIE, DISPERBYK), a solution of alkylol ammonium of a multifunctional polymer (BYK-CHEMIE, DISPERBYK-181), and mixtures of the foregoing dispersants.

Specific examples of complex, larger molecular weight dispersants include, but are not limited to, siloxanes, such as a polyester siloxane copolymer (TEGO, WET KL 245/WET 260), and hydrophilic polymers having the structure of AB or BAB type, wherein A is a hydrophobic homopolymer or copolymer of an unsubstituted or substituted $C_1$–$C_{30}$ acrylic monomer and B is a hydrophilic polymer or copolymer of a unsubstituted or substituted $C_1$–$C_{30}$ acrylic polymer. More specific examples of the complex, larger molecular weight dispersants include, but are not limited to, an acrylic acid/acrylate copolymer, a methacrylic acid/methacrylate copolymer, an acrylic acid/polydialkylsiloxane/acrylate block copolymer, and a mixture of the foregoing polymers.

In each of the above-described ink compositions according to embodiments of the present invention, the amount of the dispersant may be in the range of 0.1–20 parts by weight with respect to 100 parts by weight of the ink composition.

The viscosity adjuster in each of the ink compositions adjusts the viscosity of the ink composition for smoother jetting. Specific examples of such a viscosity adjuster include, but are not limited to, casein, hydroxymethylcellulose, hydroxyethylcellulose, carboxymethylcellulose, and the like. The amount of the viscosity adjuster may be in the range of 0.1–5.0 parts by weight with respect to 100 parts by weight of the ink composition.

In each of the above ink compositions according to embodiments of the present invention, the amount of the dispersant may be in the range of 1–20 parts by weight with respect to 100 parts by weight of the ink composition.

The viscosity adjuster of each of the ink compositions adjusts the viscosity of the ink composition for smoother jetting. Specific examples of such a viscosity adjuster include, but are not limited to, casein, carboxymethylcellulose, and the like. The amount of the viscosity adjuster may be in the range of 0.1–5 parts by weight with respect to 100 parts by weight of the ink composition.

In each of the above ink compositions according to an embodiment of the present invention, the amount of the surfactant may be in the range of 0.1–5 parts by weight with respect to 100 parts by weight of the ink composition. The surfactant of each of the ink compositions affects the surface tension of the composition such that the ink composition is more stably jetted through a nozzle. An anionic surfactant or a nonionic surfactant may be used.

Examples of an anionic surfactant that may be used in the present invention include, but are not limited to, a salt of alkylcarboxylic acid having 1 to 1,000 carbon atoms, preferably, 10 to 200 carbon atoms, a salt of alcohol sulfonic acid ester having 1 to 1,000 carbon atoms, preferably, 10 to 200 carbon atoms, a salt of alkylsulfonic acid having 1 to 1,000 carbon atoms, preferably, 10 to 200 carbon atoms, a salt of alkylbenzene sulfonic acid having 1 to 1,000 carbon atoms, preferably, 10 to 200 carbon atoms, and a mixture of the foregoing salts.

Examples of a nonionic surfactant that may be used in the present invention include, but are not limited to, polyoxyethylene alkyl ether having a $C_1$–$C_{1000}$, preferably, $C_{10}$–$C_{200}$, alkyl group, polyoxyethylene alkyl phenyl ether having a $C_1$–$C_{1000}$, preferably, $C_{10}$–$C_{200}$, alkyl group, polyoxyethylene secondary alkyl ether, a polyoxyethylene-oxypropylene block copolymer, polyglycerin fatty acid ester, a sorbitan fatty acid ester, and a mixture of the foregoing materials.

In each of the above ink compositions according to embodiments of the present invention, the amount of the surfactant may be in the range of 0.1–5 parts by weight with respect to 100 parts by weight of the ink composition.

The wetting agent of each of the ink compositions prevents nozzles from clogging. A polyhydric alcohol may be used as the wetting agent. Specific examples of a wetting agent that may be used in the present invention include, but are not limited to, glycerin, ethylene glycol, diethylene glycol, triethylene glycol, propylene glycol, dipropylene glycol, hexylene glycol, 1,3-butane diol, 1,4-butane diol, 1,5-pentanediol, 2-butene-1,4-diol, and a mixture of the foregoing alcohols. In each of the above ink compositions according to embodiments of the present invention, the amount of the wetting agent may be in the range of 10–30 parts by weight with respect to 100 parts by weight of the ink composition.

In each of the above ink compositions according to embodiments of the present invention, the total amount of at least one additive selected from the group consisting of a dispersant, a viscosity adjuster, a surfactant, a storage stabilizer, and a wetting agent may be in the range of 0.5–40 parts by weight with respect to 100 parts by weight of the ink composition.

A method of preparing the above ink compositions, according to an embodiment of the present invention, will now be described.

The lightfast colorant and/or a general colorant and other additives, for example, a dispersant, a viscosity adjuster, a surfactant, and the like, are mixed together in an aqueous medium and thoroughly stirred to obtain a homogeneous composition. This composition is passed through a filter having a pore size of 0.45–0.8 μm to obtain an ink composition according to an embodiment of the present invention.

Regarding the lightfast colorant according to an embodiment of the present invention, its sulfonic acid group (—$SO_3H$) may include a metallic sulfonate group, such as a sodium sulfonate group (—$SO_3Na$).

The present invention will be described in greater detail with reference to the following examples. The following examples are for illustrative purposes and are not intended to limit the scope of the invention.

Synthesis Example 1

2-hydroxy-4-(4-carboxy)phenyloxybenzophenone was synthesized according to reaction scheme (5) below.

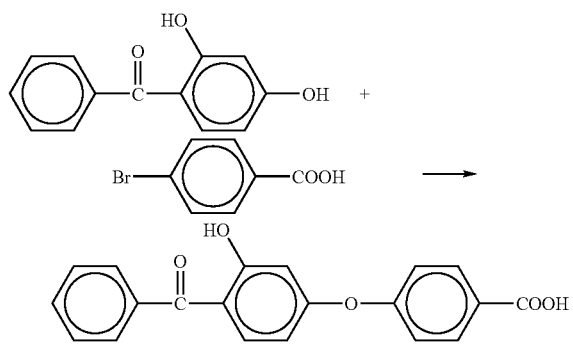

Reaction scheme (5)

A 250-mL round-bottomed flask equipped with a reflux condenser was charged with 150 mL of dimethylformamide (DMF) and 10.7 g of 2,4-dihydxoxybenzophenone, and 1.2 g of sodium hydride was added while supplying nitrogen into the flask and stirred. 10 g of 4-bromobenzoic acid was slowly added into the mixture, heated slowly to about 60° C. while stirring it, and reacted for 5 hours. The reaction mixture was cooled to room temperature, and the reaction product was poured into excess distilled water to precipitate. The resulting precipitates were filtered, washed several times with distilled water, and recrystallized using a solvent mixture of chloroform and ethanol to provide 9.5 g of 2-hydroxy-4-(4-carboxy)phenyloxybenzophenone.

Synthesis Example 2

2-hydroxy-4-(8-carboxy)octyloxybenzophenone was synthesized according to reaction scheme (6) below.

Reaction scheme (6)

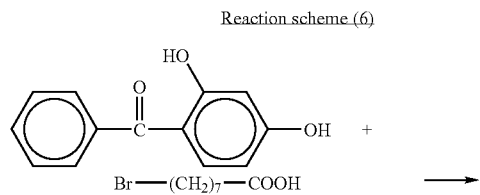

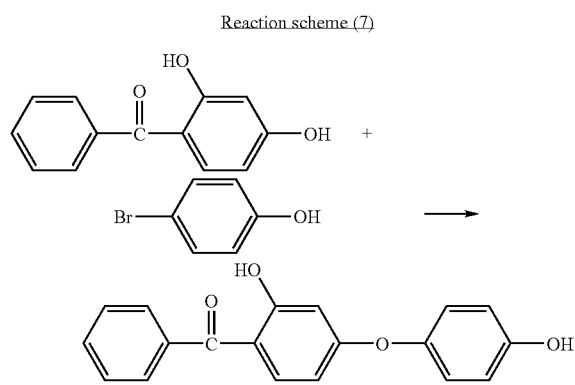

10 g of 2-hydroxy-4-(8-carboxy)octyloxybenzophenone was synthesized in the same manner as in Synthesis Example 1, except that 11.5 g of 8-bromooctanoic acid was used instead of 10 g of 4-bromobenzoic acid.

Synthesis Example 3

2-hydroxy-4-(4-hydroxy)phenyloxybenzophenone was synthesized according to reaction scheme (7) below.

Reaction scheme (7)

9.7 g of 2-hydroxy-4-(4-hydroxy)phenyloxybenzophenone was synthesized in the same manner as in Synthesis Example 1, except that 8.7 g of 4-bromophenol was used instead of 10 g of 4-bromobenzoic acid.

Synthesis Example 4

2-hydroxy-4-(6-hydroxy)hexyloxybenzophenone was synthesized according to reaction scheme (8) below.

Reaction scheme (8)

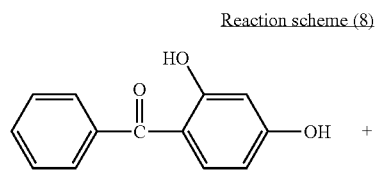

-continued

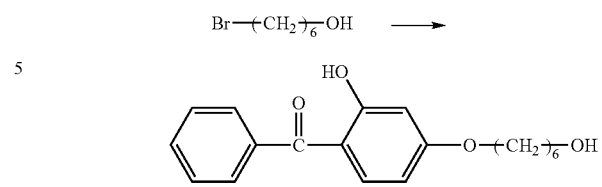

10.6 g of 2-hydroxy-4-(6-hydroxy)hexyloxybenzophenone was synthesized in the same manner as in Synthesis Example 1, except that 9.1 g of 6-bromo-1-hexanol was used instead of 10 g of 4-bromobenzoic acid.

Synthesis Example 5

2-hydroxy-4-(4-amino)phenyloxybenzophenone was synthesized according to reaction scheme (9) below.

Reaction scheme (9)

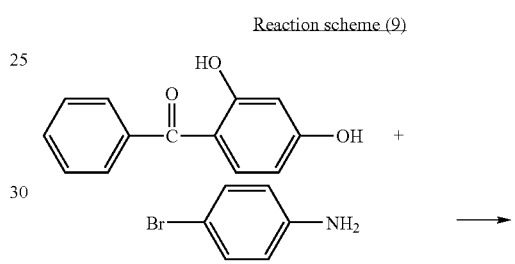

10.3 g of 2-hydroxy-4-(4-amino)phenyloxybenzohenone was synthesized in the same manner as in Synthesis Example 1, except that 8.6 g of 4-bromoaniline was used instead of 10 g of 4-bromobenzoic acid.

Synthesis Example 6

A lightfast colorant of formula (9) below was synthesized by reacting the benzophenone derivative obtained in Synthesis Example 1 with a direct dye C.I. DIRECT BLACK 168.

A 250-mL round-bottomed flask equipped with a reflux condenser was charged with 150 mL of an ethyl acetate solvent, 8.3 g of the benzophenone derivative obtained in Synthesis Example 1, and 16.6 g of C.I. DIRECT BLACK 168, and the reactants were dissolved in the solvent. 10 mL of conc. sulfuric acid was slowly added together with one or two boiling chips into the mixture and refluxed for 12 hours or longer. The reaction product was washed with distilled water and the organic phase was collected. This organic phase was concentrated and recrystallized to provide 16.5 g of the lightfast colorant of formula (9).

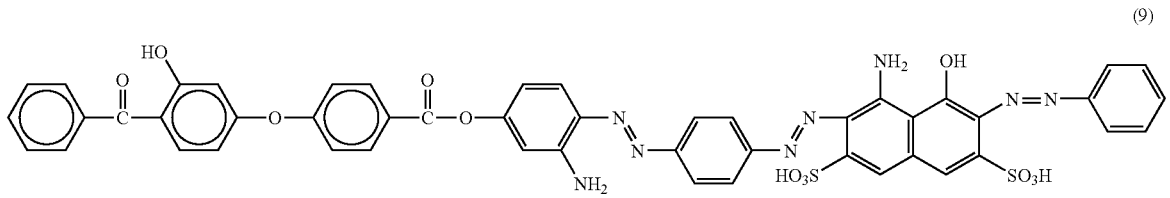

(9)

Synthesis Example 7

A lightfast colorant of formula (10) below was synthesized by reacting the benzophenone derivative obtained in Synthesis Example 1 with an acid dye ACID YELLOW 23.

8.3 g of the benzophenone derivative obtained in Synthesis Example 1 was dissolved in 200 mL of dimethylsulfoxide (DMSO) in a 500-mL round-bottomed flask equipped with a reflux. 3.0 g of $SOCl_2$ was added to the mixture and reacted at room temperature for 1 hour or longer. A solution of 12.3 g of C.I. ACID YELLOW 23 in 200 mL of DMSO was added into the flask together with one or two boiling chips and reacted at 80° C. for 8 hours or longer. The reaction product was cooled to room temperature, and an excess of methanol was added to precipitate a desired crystalline compound. The crystalline precipitates were filtered by suction and washed. To remove unreacted products, the crystalline compound was dissolved in DMSO and precipitated with methanol. The resulting crystalline precipitates were filtered by suction, washed, and dried in an oven to provide 12.7 g of the lightfast colorant of formula (10).

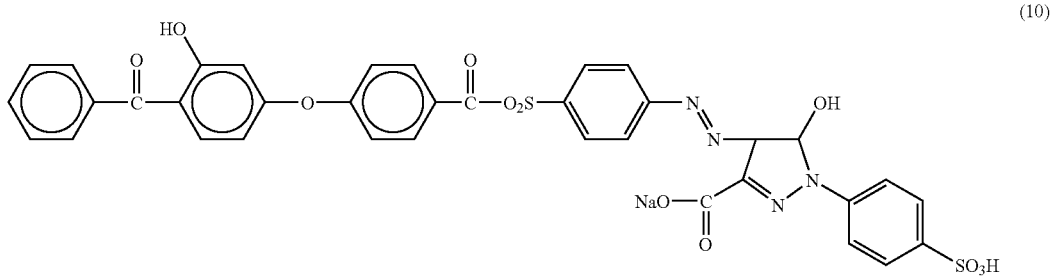

(10)

Synthesis Example 8

A lightfast colorant of formula (11) below was synthesized by reacting the benzophenone derivative obtained in Synthesis Example 2 with the direct dye C.I. DIRECT BLACK 168.

A 250-mL round-bottomed flask equipped with a reflux condenser was charged with 150 mL of an ethyl acetate solvent, 8.9 g of the benzophenone derivative obtained in Synthesis Example 2, and 16.6 g of C.I. DIRECT BLACK 168, and the reactants were dissolved in the solvent.

10 mL of conc. sulfuric acid was slowly added together with one or two boiling chips into the mixture and refluxed for 12 hours or longer. The reaction product was washed with distilled water, and the organic phase was collected. This organic phase was concentrated and recrystallized to provide 17.3 g of the lightfast colorant of formula (11).

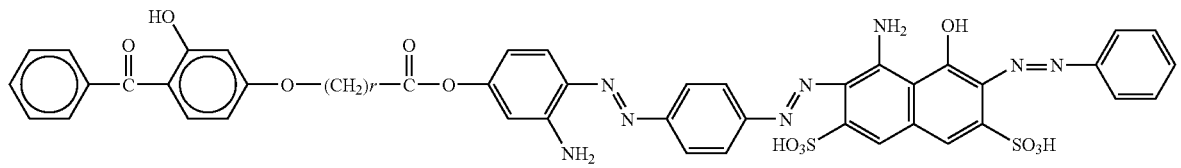

(11)

Synthesis Example 9

A lightfast colorant of formula (12) below was synthesized by reacting the benzophenone derivative obtained in Synthesis Example 2 with an acid dye C.I. ACID BLACK 191.

8.9 g of the benzophenone derivative obtained in Synthesis Example 2 was dissolved in 150 mL of DMSO in a 500-mL round-bottomed flask equipped with a reflux condenser. 3.0 g of $SOCl_2$ was added to the mixture and reacted at room temperature for 1 hour or longer.

A solution of 19.3 g of C.I. ACID BLACK 191 in 200 mL of DMSO was added into the flask, together with one or two boiling chips and reacted at 80° C. for 8 hours or longer. The reaction product was cooled to room temperature, and excess methanol was added to precipitate a desired crystalline compound. The crystalline precipitates were filtered by suction and washed. To remove unreacted products, the crystalline compound was dissolved in DMSO and precipitated with methanol. The resulting crystalline precipitates were filtered by suction, washed, and dried in an oven to provide 18.5 g of the lightfast colorant of formula (12).

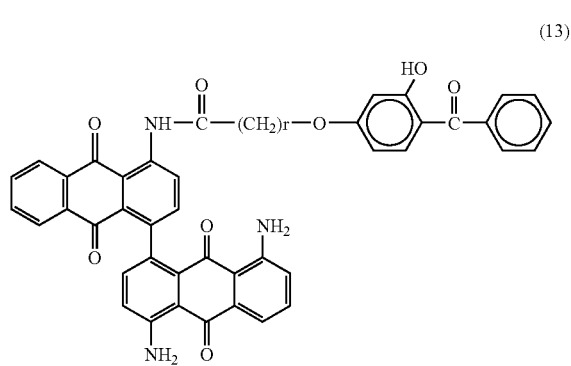

(13)

Synthesis Example 11

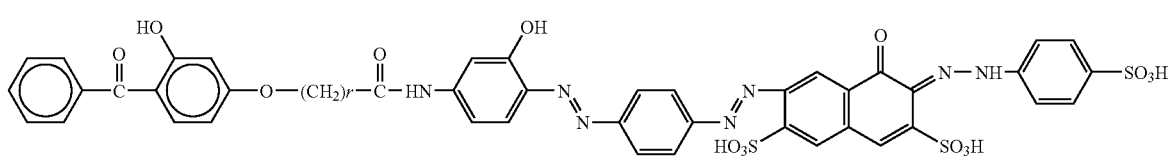

(12)

Synthesis Example 10

A lightfast colorant of formula (13) below was synthesized by reacting the benzophenone derivative obtained in Synthesis Example 2 with C.I. PIGMENT RED 177.

8.9 g of the benzophenone derivative obtained in Synthesis Example 2 was dissolved in 150 mL of DMSO in a 500-mL round-bottomed flask equipped with a reflux condenser. 3.0 g of $SOCl_2$ was added to the mixture and reacted at room temperature for 1 hour or longer. A solution of 8.7 g of C.I. PIGMENT RED 177 in 200 mL of DMSO was added to the flask together with one or two boiling chips and reacted at 80° C. for 8 hours or longer. The reaction product was cooled to room temperature, and excess methanol was added to precipitate a desired crystalline compound. The crystalline precipitates were filtered by suction and washed. To remove unreacted products, the crystalline compound was dissolved in DMSO and precipitated with methanol. The resulting crystalline precipitates were filtered by suction, washed, and dried in an oven to provide 13.3 g of the lightfast colorant of formula (13).

A lightfast colorant of formula (14) below was synthesized by reacting the benzophenone derivative obtained in Synthesis Example 3 with a direct dye C.I. DIRECT BLACK 51.

14.3 g of C.I. DIRECT BLACK 51 was dissolved in 150 mL of DMSO in a 500-mL round-bottomed flask equipped with a reflux condenser. 3.0 g of $SOCl_2$ was added to the mixture and reacted at room temperature for 1 hour or longer. A solution of 7.6 g of the benzophenone derivative obtained in Synthesis Example 3 in 200 mL of DMSO was added into the flask together with one or two boiling chips and reacted at 80° C. for 8 hours or longer. The reaction product was cooled to room temperature, and excess methanol was added to precipitate a desired crystalline compound. The crystalline precipitates were filtered by suction and washed. To remove unreacted products, the crystalline compound was dissolved in DMSO and precipitated with methanol. The resulting crystalline precipitates were filtered by suction, washed, and dried in an oven to provide 14.7 g of the lightfast colorant of formula (14).

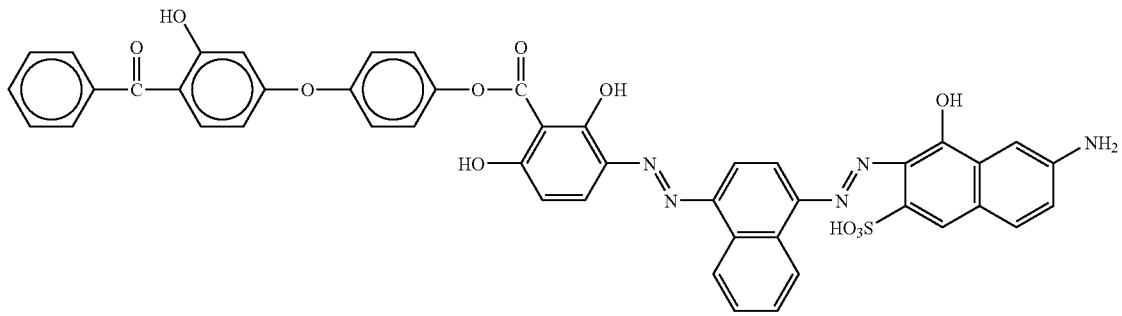

(14)

Synthesis Example 12

A lightfast colorant of formula (15) below was synthesized by reacting the benzophenone derivative obtained in Synthesis Example 4 with the direct dye C.I. DIRECT BLACK 51.

14.3 g of C.I. DIRECT BLACK 51 was dissolved in 150 mL of DMSO in a 500-mL round-bottomed flask equipped with a reflux condenser. 3.0 g of $SOCl_2$ was added to the mixture and reacted at room temperature for 1 hour or longer. A solution of 7.9 g of the benzophenone derivative obtained in Synthesis Example 4 in 200 mL of DMSO was added to the flask together with one or two boiling chips and reacted at 80° C. for 8 hours or longer. The reaction product was cooled to room temperature, and excess methanol was added to precipitate a desired crystalline compound. The crystalline precipitates were filtered by suction and washed. To remove unreacted products, the crystalline compound was dissolved in DMSO and precipitated with methanol. The resulting crystalline precipitates were filtered by suction, washed, and dried in an oven to provide 15.7 g of the lightfast colorant of formula (15).

Synthesis Example 13

A lightfast colorant of formula (16) below was synthesized by reacting the benzophenone derivative obtained in Synthesis Example 4 with C.I. PIGMENT RED 57.

10.2 g of C.I. PIGMENT RED 57 was dissolved in 150 mL of DMSO in a 500-mL round-bottomed flask equipped with a reflux condenser. 3.0 g of $SOCl_2$ was added to the mixture and reacted at room temperature for 1 hour or longer. A solution of 7.9 g of the benzophenone derivative obtained in Synthesis Example 4 in 200 mL of DMSO was added to the flask together with one or two boiling chips and reacted at 80° C. for 8 hours or longer. The reaction product was cooled to room temperature, and excess methanol was added to precipitate a desired crystalline compound. The crystalline precipitates were filtered by suction and washed. To remove unreacted products, the crystalline compound was dissolved in DMSO and precipitated with methanol. The resulting crystalline precipitates were filtered by suction, washed, and dried in an oven to provide 11.5 g of the lightfast colorant of formula (16).

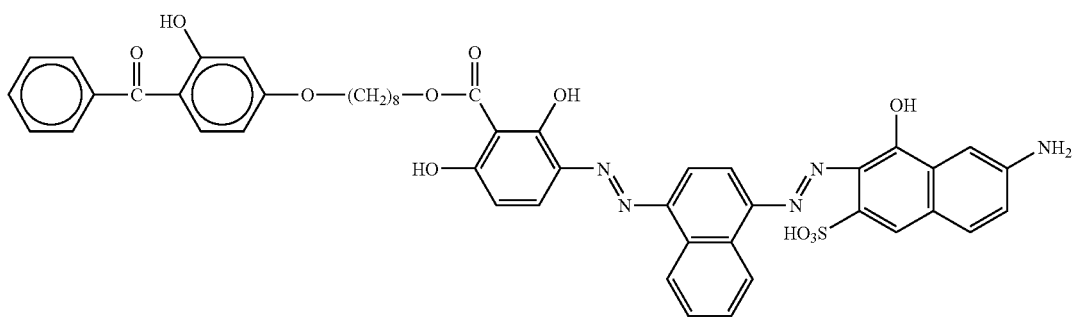

(15)

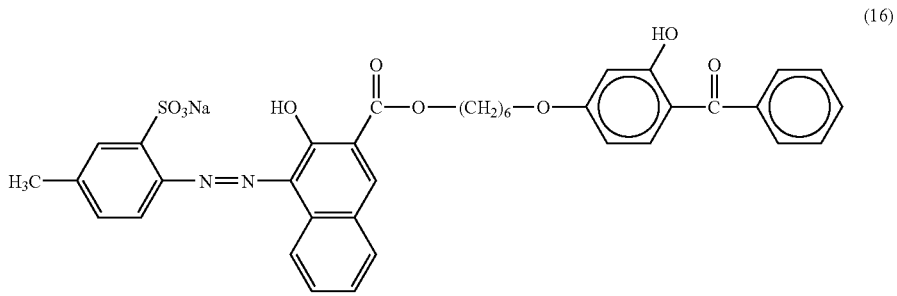

(16)

Synthesis Example 14

A lightfast colorant of formula (17) below was synthesized by reacting the benzophenone derivative obtained in Synthesis Example 5 with C.I. PIGMENT RED 57.

10.2 g of C.I. PIGMENT RED 57 was dissolved in 150 mL of DMSO in a 500-mL round-bottomed flask equipped with a reflux condenser. 3.0 g of $SOCl_2$ was added to the mixture and reacted at room temperature for 1 hour or longer. A solution of 7.5 g of the benzophenone derivative obtained in Synthesis Example 5 in 200 mL of DMSO was added to the flask together with one or two boiling chips and reacted at 80° C. for 8 hours or longer. The reaction product was cooled to room temperature, and excess methanol was added to precipitate a desired crystalline compound. The crystalline precipitates were filtered by suction and washed. To remove unreacted products, the crystalline compound was dissolved in DMSO and precipitated with methanol. The resulting crystalline precipitates were filtered by suction, washed, and dried in an oven to provide 12.5 g of the lightfast colorant of formula (17).

Example 1

Ink Composition

| COMPONENT | CONTENT |
| --- | --- |
| C.I. DIRECT BLACK 168 | 3 g |
| Lightfast Colorant of Synthesis Example 6 | 1 g |
| Water | 77 g |
| Isopropyl alcohol | 3 g |
| Ethylene glycol | 10 g |
| Glycerin | 6 g |

The above-listed components were mixed together and stirred for about 30 minutes or longer to obtain a homogeneous composition. This composition was passed through a 0.45-μm filter to provide a lightfast ink composition according to an embodiment of the present invention.

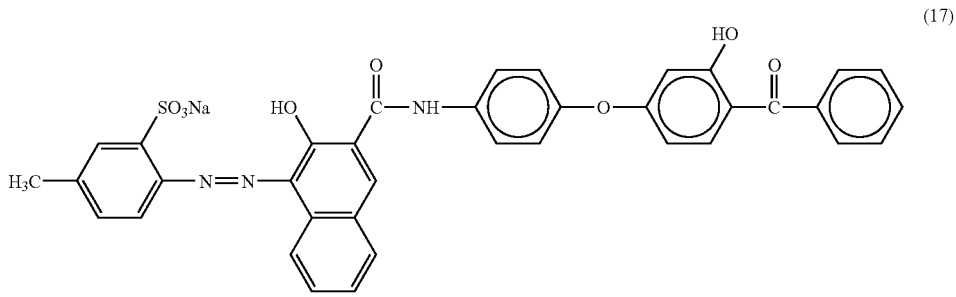

(17)

Example 2

A lightfast ink composition according to an embodiment of the present invention was prepared in the same manner as in Example 1, except that C.I. ACID YELLOW 23 instead of C.I. DIRECT BLACK 168 and the lightfast colorant obtained in Synthesis Example 7 instead of the lightfast colorant obtained in Synthesis Example 6 were used.

Example 3

A lightfast ink composition according to an embodiment of the present invention was prepared in the same manner as in Example 1, except that the lightfast colorant obtained in Synthesis Example 8 instead of the lightfast colorant obtained in Synthesis Example 6 was used.

Example 4

A lightfast ink composition according to an embodiment of the present invention was prepared in the same manner as in Example 1, except that C.I. ACID BLACK 191 instead of C.I. DIRECT BLACK 168 and the lightfast colorant obtained in Synthesis Example 9 instead of the lightfast colorant obtained in Synthesis Example 6 were used.

Example 5

Ink Composition

| COMPONENT | CONTENT |
| --- | --- |
| C.I. PIGMENT RED 177 | 3 g |
| Lightfast Colorant of Synthesis Example 10 | 1 g |
| Water | 73 g |
| Glycerin | 4 g |
| 1,5 pentanediol | 8 g |
| 2-pyrrolidone | 6 g |
| TEGO DISPERSE 750 W | 5 g |

The above-listed components were mixed together and stirred for about 30 minutes or longer to obtain a homogeneous composition. This composition was passed through a 0.8-µm filter to provide a lightfast ink composition according to an embodiment of the present invention.

Example 6

A lightfast ink composition according to an embodiment of the present invention was prepared in the same manner as in Example 1, except that C.I. DIRECT BLACK 51 instead of C.I. DIRECT BLACK 168 and the lightfast colorant obtained in Synthesis Example 11 instead of the lightfast colorant obtained in Synthesis Example 6 were used.

Example 7

A lightfast ink composition according to an embodiment of the present invention was prepared in the same manner as in Example 1, except that C.I. DIRECT BLACK 51 instead of C.I. DIRECT BLACK 168 and the lightfast colorant obtained in Synthesis Example 12 instead of the lightfast colorant obtained in Synthesis Example 6 were used.

Example 8

Ink Composition

| COMPONENT | CONTENT |
| --- | --- |
| C.I. PIGMENT RED 57 | 3 g |
| Lightfast Colorant of Synthesis Example 13 | 1 g |
| Water | 73 g |
| Glycerin | 4 g |
| Diethylene glycol | 8 g |
| 2-pyrrolidone | 6 g |
| TEGO DISPERSE 750 W | 5 g |

The above-listed components were mixed together and stirred for about 30 minutes or longer to obtain a homogeneous composition. This composition was passed through a 0.8-µm filter to provide a lightfast ink composition according to an embodiment of the present invention.

Example 9

A lightfast ink composition according to an embodiment of the present invention was prepared in the same manner as in Example 8, except that the lightfast colorant obtained in Synthesis Example 14 instead of the lightfast colorant obtained in Synthesis Example 13 was used.

Example 10

A lightfast ink composition according to an embodiment of the present invention was prepared in the same manner as in Example 1, except that 4 g of the lightfast colorant obtained in Synthesis Example 6 was used alone as the colorant component, without using C.I. DIRECT BLACK 168.

Comparative Example 1

An ink composition was prepared in the same manner as in Example 1, except that 4 g of C.I. DIRECT BLACK 168 was used alone as the colorant component, without using the lightfast colorant of Synthesis Example 6.

Comparative Example 2

An ink composition was prepared in the same manner as in Example 2, except that 4 g of C.I. ACID YELLOW 23 was used alone as the colorant component, without using the lightfast colorant of Synthesis Example 7.

Comparative Example 3

An ink composition was prepared in the same manner as in Example 4, except that 4 g of C.I. ACID BLACK 191 was used alone as the colorant component, without using the lightfast colorant of Synthesis Example 9.

Comparative Example 4

An ink composition was prepared in the same manner as in Example 6, except that 4 g of C.I. DIRECT BLACK 51 was used alone as the colorant component, without using the lightfast colorant of Synthesis Example 11.

Comparative Example 5

An ink composition was prepared in the same manner as in Example 5, except that 4 g of C.I. PIGMENT RED 177 was used alone as the colorant component, without using the lightfast colorant of Synthesis Example 10.

Comparative Example 6

An ink composition was prepared in the same manner as in Example 8, except that 4 g of C.I. PIGMENT RED 57 was used alone as the colorant component, without using the lightfast colorant of Synthesis Example 13.

Comparative Example 7

An ink composition was prepared in the same manner as in Comparative Example 1, except that 0.2 g of octyl-methoxybenzophenone was further added as a lightfastness enhancer.

Comparative Example 8

An ink composition was prepared in the same manner as in Comparative Example 2, except that 0.2 g of octyl-methoxybenzophenone was further added as a lightfastness enhancer.

Comparative Example 9

An ink composition was prepared in the same manner as in Comparative Example 3, except that 0.2 g of octyl-methoxybenzophenone was further added as a lightfastness enhancer.

Comparative Example 10

An ink composition was prepared in the same manner as in Comparative Example 4, except that 0.2 g of octyl-methoxybenzophenone was further added as a lightfastness enhancer.

The lightfastness and the anti-clogging property of the ink compositions prepared in the above examples and comparative examples were evaluated as follows.

Storage Stability (Anti-Clogging Property) Test 100 mL of samples of the ink compositions prepared in Examples 1 through 10 and Comparative Examples 1 through 10 were portioned into respective heat-resistant glass bottles. The glass bottles were sealed and stored in a 60° C.-water bath for 2 months. It was observed whether precipitates appeared in the bottles. The results are shown in Table 1. In Table 1, 0 indicates that no precipitate appeared, and X indicates that precipitates appeared.

TABLE 1

| No. | Example | | | | | | | | | | Comparative Example | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 1 | 2 | 3 | 4 | 5 | 6 | 7 | 8 | 9 | 10 |
| Result | 0 | 0 | 0 | 0 | 0 | 0 | 0 | 0 | 0 | 0 | 0 | 0 | 0 | 0 | 0 | 0 | X | X | X | X |

As shown in Table 1, for the ink compositions prepared in Examples 1 through 10, which contain the lightfast colorants according to embodiments of the present invention, no precipitates appear, indicating that the ink compositions according to embodiments of the present invention have better long-term storage stability than the ink compositions of Comparative Examples 7 through 10, that contain the conventional colorants and the lightfastness enhancer and precipitate.

Lightfastness Test

2×2 cm solid patterns were printed using the ink compositions of Examples 1 through 10 and Comparative Examples 1 through 10 and an ink jet printer (MJC 1130i, available from SAMSUNG ELECTRONICS CO.). The printed results were exposed to light for 100 hours in a Q-SUN XENON TEST CHAMBER. Optical density (OD) was measured before and after light exposure, and A values (lightfastness values) were calculated using the following equation. Lightfastness was evaluated as good (G) for $A \geq 90$, moderate (M) for $75 \leq A < 90$, and poor (X) for $A < 75$. The results are shown in Table 2.

$A = OD$ after exposure/$OD$ before exposure×100(%)

TABLE 2

| No. | Example | | | | | | | | | | Comparative Example | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 1 | 2 | 3 | 4 | 5 | 6 | 7 | 8 | 9 | 10 |
| Result | G | G | G | G | G | G | G | G | G | G | X | X | X | X | M | M | G | G | G | G |

As shown in Table 2, the ink compositions prepared in Examples 1 through 10, which contain the lightfast colorants according to embodiments of the present invention, have improved lightfastness at A values of 90% or more. However, the ink compositions prepared in Comparative Examples 1 through 6, which contain the conventional colorants, have lightfastness values of less than 90%. Evidently, the ink compositions according to embodiments of the present invention have improved lightfastness compared to the conventional ink compositions.

As described above, lightfast colorants according to embodiments of the present invention, which are derived by covalently binding a lightfast benzophenone derivative and a conventional colorant, have improved lightfastness. When such a lightfast colorant according to an embodiment of the present invention is added to an ink composition, the storage stability as well as the lightfastness of the ink composition are improved.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A lightfast ink composition comprising:
at least one lightfast colorant that is a benzophenone derivative of formula (1) below:

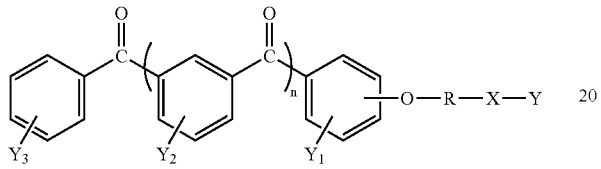

(1)

wherein $Y_1$ is one selected from the group consisting of —H, —OH, —$NH_2$, —$NHR_1$, —$N(R_1)_2$, —SH, and a $C_1$–$C_{30}$ heteroalkyl group, where $R_1$ is a $C_1$–$C_6$ alkyl group;

each of $Y_2$ and $Y_3$ is independently selected from the group consisting of —H, —OH, —$NH_2$, —$NHR_1$, —$N(R_1)_2$, where $R_1$ is a $C_1$–$C_6$ alkyl group, —SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

n is an integer from 0 to 6;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —CONH—, —NHCO—, —COO—, —OCO—, —CO—, —O—, —S—, —$SO_2$—, —$SO_3$—, —O—P(=O)(OH)—O—, and —O—P(OH)—O—; and Y is a colorant residue; and an aqueous medium.

2. The lightfast ink composition of claim 1, wherein the amount of the lightfast colorant is in the range of 0.1–20 parts by weight with respect to 100 parts by weight of the ink composition.

3. A lightfast ink composition comprising:
a colorant;
at least one lightfast colorant that is a benzophenone derivative of formula (1) below:

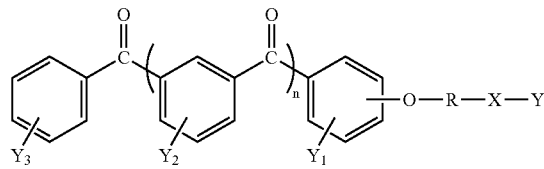

(1)

wherein $Y_1$ is one selected from the group consisting of —H, —OH, —$NH_2$, —$NHR_1$, —$N(R_1)_2$, —SH, and a $C_1$–$C_{30}$ heteroalkyl group, where $R_1$ is a $C_1$–$C_6$ alkyl group;

each of $Y_2$ and $Y_3$ is independently selected from the group consisting of —H, —OH, —$NH_2$, —$NHR_1$, —$N(R_1)_2$, where $R_1$ is a $C_1$–$C_6$ alkyl group, —SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

n is an integer from 0 to 6;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —CONH—, —NHCO—, —COO—, —OCO—, —CO—, —O—, —S—, —$SO_2$—, —$SO_3$—, —O—P(=O)(OH)—O—, and —O—P(OH)—O—; and Y is a colorant residue; and an aqueous medium.

4. The lightfast ink composition of claim 3, wherein the amount of the colorant is in the range of 1–25 parts by weight, the amount of the lightfast colorant is in the range of 0.1–20 parts by weight, and the total amount of the colorant and the lightfast colorant is in the range of 1.1–45 parts by weight, with respect to 100 parts by weight of the lightfast ink composition.

5. The lightfast ink composition of claim 1, wherein the aqueous medium is one of water and a mixture of 5–10% by weight of an organic solvent and 50–95% by weight of water.

6. The lightfast ink composition of claim 5, wherein the organic solvent is selected from the group consisting of methyl alcohol, ethyl alcohol, n-propyl alcohol, isopropyl alcohol, n-butyl alcohol, sec-butyl alcohol, t-butyl alcohol, isobutyl alcohol, acetone, methylethyl ketone, diacetone alcohol, methyl acetate, ethyl acetate, ethyl lactate, ethylene glycol, diethylene glycol, triethylene glycol, propylene glycol, butylene glycol, 1,4-butane diol, 1,2,4-butane triol, 1,5-pentanediol, 1,2,6-hexane triol, hexylene glycol, glycerol, glycerol ethoxylate, trimethylolpropane ethoxylate, ethylene glycol monomethyl ether, ethylene glycol monoethyl ether, diethylene glycol methyl ether, diethylene glycol ethyl ether, triethylene glycol monomethyl ether, triethylene glycol monoethyl ether, 2-pyrrolidone, N-methyl-2-pyrrolidone, dimethyl sulfoxide, tetramethylene sulfone, and thioglycol.

7. The lightfast ink composition of claim 1, further comprising at least one additive selected from the group consisting of a dispersant, a viscosity adjuster, a surfactant, a storage stabilizer, and a wetting agent, wherein the amount of the at least one additive is in a range of 0.5–40 parts by weight with respect to 100 parts by weight of the lightfast ink composition.

8. The lightfast ink composition of claim 3, wherein the aqueous medium is one of water and a mixture of 5–10% by weight of an organic solvent and 50–95% by weight of water.

9. The lightfast ink composition of claim 3, further comprising at least one additive selected from the group consisting of a dispersant, a viscosity adjuster, a surfactant, a storage stabilizer, and a wetting agent, wherein the amount of the at least one additive is in a range of 0.5–40 parts by weight with respect to 100 parts by weight of the lightfast ink composition.

10. The lightfast ink composition of claim 1, comprising:
at least one lightfast colorant of formula (3) below:

substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

n is an integer from 0 to 6;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —CONH—, —NHCO—, —COO—, —OCO—, —CO—, —O—, —S—, —$SO_2$—, —$SO_3$—, —O—P(=O)(OH)—O—, and —O—P(OH)—O—; and an aqueous medium.

11. The lightfast ink composition of claim 1, comprising:
at least one lightfast colorant of formula (4) below:

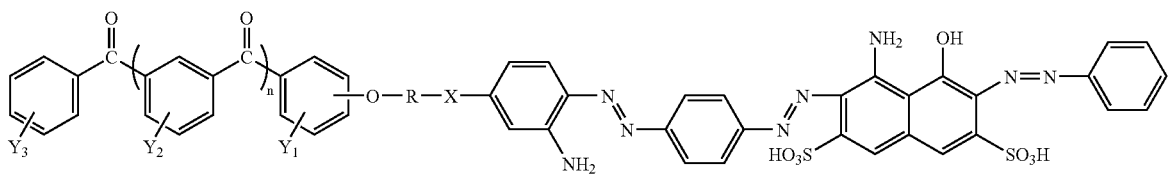

(3)

wherein $Y_1$ is one selected from the group consisting of —H, —OH, —$NH_2$, —$NHR_1$, —$N(R_1)_2$, —SH, and a $C_1$–$C_{30}$ heteroalkyl group, where $R_1$ is a $C_1$–$C_6$ alkyl group;

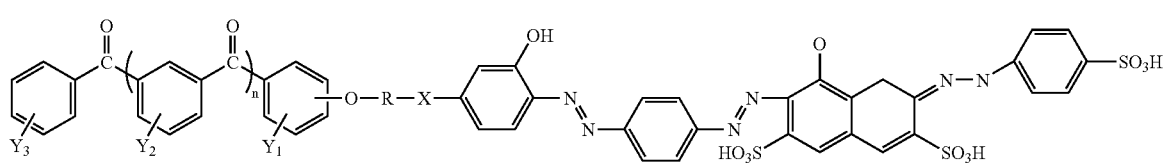

(4)

each of $Y_2$ and $Y_3$ is independently selected from the group consisting of —H, —OH, —$NH_2$, —$NHR_1$, —$N(R_1)_2$, where $R_1$ is a $C_1$–$C_6$ alkyl group, —SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a wherein $Y_1$ is one selected from the group consisting of —H, —OH, —$NH_2$, —$NHR_1$, —$N(R_1)_2$, —SH, and a $C_1$–$C_{30}$ heteroalkyl group, where $R_1$ is a $C_1$–$C_6$ alkyl group;

each of $Y_2$ and $Y_3$ is independently selected from the group consisting of —H, —OH, —$NH_2$, —$NHR_1$, —$N(R_1)_2$, where $R_1$ is a $C_1$–$C_6$ alkyl group, —SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

n is an integer from 0 to 6;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —CONH—, —NHCO—, —COO—, —OCO—, —CO—, —O—, —S—, —SO$_2$—, —SO$_3$—, —O—P(=O)(OH)—O—, and —O—P(OH)—O—; and an aqueous medium.

12. The lightfast ink composition of claim 1, comprising: at least one lightfast colorant of formula (5) below:

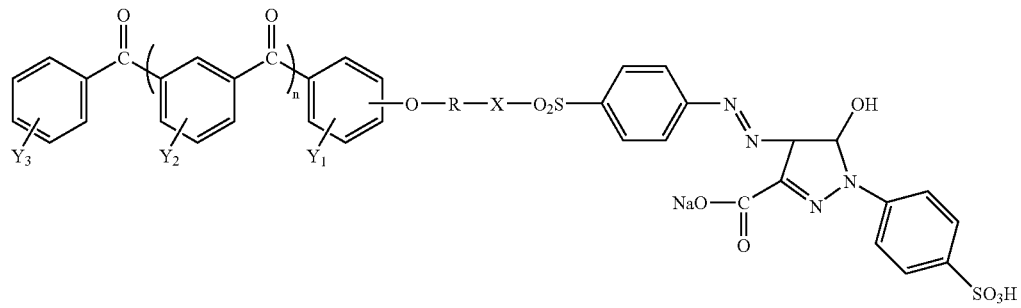

(5)

wherein $Y_1$ is one selected from the group consisting of —H, —OH, —NH$_2$, —NHR$_1$, —N(R$_1$)$_2$, —SH, and a $C_1$–$C_{30}$ heteroalkyl group, where $R_1$ is a $C_1$–$C_6$ alkyl group;

each of $Y_2$ and $Y_3$ is independently selected from the group consisting of —H, —OH, —NH$_2$, —NHR$_1$, —N(R$_1$)$_2$, where $R_1$ is a $C_1$–$C_6$ alkyl group, —SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

n is an integer from 0 to 6;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —CONH—, —NHCO—, —COO—, —OCO—, —CO—, —O—, —S—, —SO$_2$—, —SO$_3$—, —O—P(=O)(OH)—O—, and —O—P(OH)—O—; and an aqueous medium.

13. The lightfast ink composition of claim 1, comprising: at least one lightfast colorant of formula (6) below:

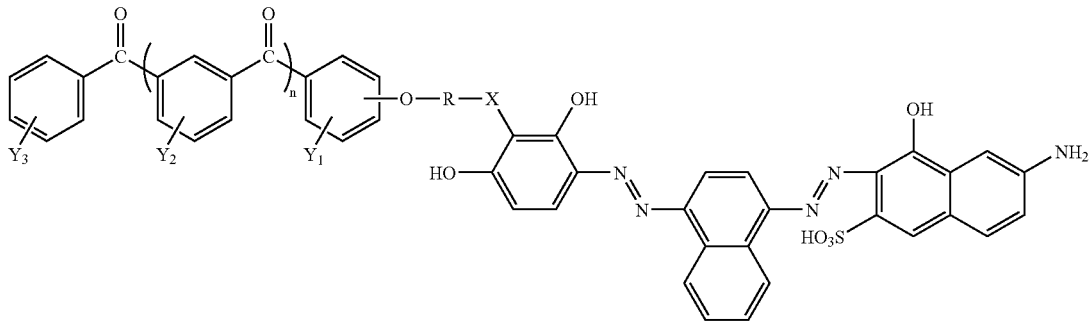

(6)

wherein $Y_1$ is one selected from the group consisting of —H, —OH, —NH$_2$, —NHR$_1$, —N(R$_1$)$_2$, —SH, and a $C_1$–$C_{30}$ heteroalkyl group, where $R_1$ is a $C_1$–$C_6$ alkyl group;

each of $Y_2$ and $Y_3$ is independently selected from the group consisting of —H, —OH, —NH$_2$, —NHR$_1$, —N(R$_1$)$_2$, where $R_1$ is a $C_1$–$C_6$ alkyl group, —SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

n is an integer from 0 to 6;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$4–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —CONH—, —NHCO—, —COO—, —OCO—, —CO—, —O—, —S—, —SO$_2$—, —SO$_3$—, —O—P(=O)(OH)—O—, and —O—P(OH)—O—; and an aqueous medium.

14. The lightfast ink composition of claim 1, comprising: at least one lightfast colorant of formula (7) below:

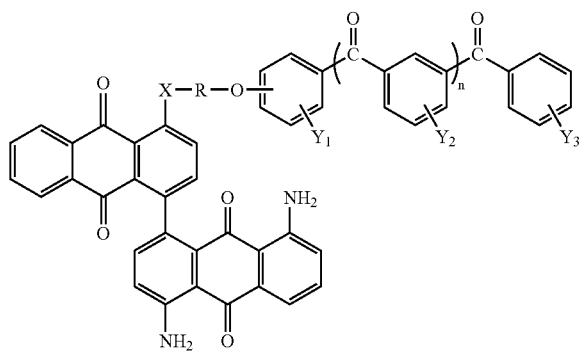

(7)

wherein $Y_1$ is one selected from the group consisting of —H, —OH, —NH$_2$, —NHR$_1$, —N(R$_1$)$_2$, —SH, and a $C_1$–$C_{30}$ heteroalkyl group, where $R_1$ is a $C_1$–$C_6$ alkyl group;

each of $Y_2$ and $Y_3$ is independently selected from the group consisting of —H, —OH, —NH$_2$, —NHR$_1$, —N(R$_1$)$_2$, where $R_1$ is a $C_1$–$C_6$ alkyl group, —SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

n is an integer from 0 to 6;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —CONH—, —NHCO—, —COO—, —OCO—, —CO—, —O—, —S—, —SO$_2$—, —SO$_3$—, —O—P(=O)(OH)—O—, and —O—P(OH)—O—; and an aqueous medium.

15. The lightfast ink composition of claim 1, comprising: at least one lightfast colorant of formula (8) below:

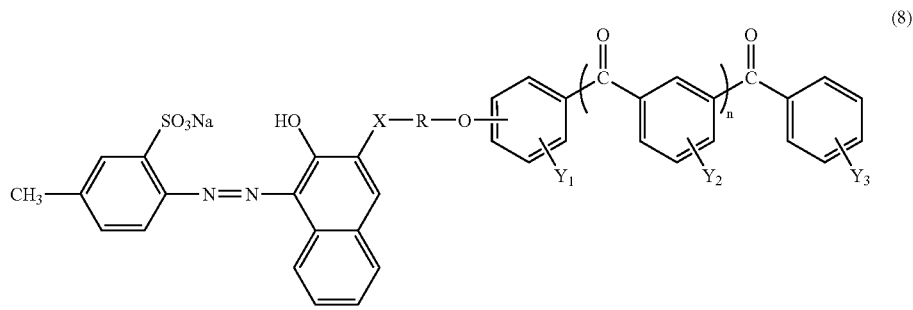

(8)

wherein $Y_1$ is one selected from the group consisting of —H, —OH, —NH$_2$, —NHR$_1$, —N(R$_1$)$_2$, —SH, and a $C_1$–$C_{30}$ heteroalky group, where $R_1$ is a $C_1$–$C_6$ alkyl group;

each of $Y_2$ and $Y_3$ is independently selected from the group consisting of —H, —OH, —NH$_2$, —NHR$_1$, —N(R$_1$)$_2$, where $R_1$ is a $C_1$–$C_6$ alkyl group, —SH, a substituted or unsubstituted $C_1$–$C_{30}$ alkyl group, a substituted or unsubstituted $C_1$–$C_{30}$ alkenyl group, a substituted or unsubstituted $C_1$–$C_{30}$ alkynyl group, a substituted or unsubstituted $C_1$–$C_{30}$ heteroalkyl group, a substituted or unsubstituted $C_6$–$C_{30}$ aryl group, a substituted or unsubstituted $C_7$–$C_{30}$ arylalkyl group, a substituted or unsubstituted $C_3$–$C_{30}$ heteroaryl group, and a substituted or unsubstituted $C_4$–$C_{30}$ heteroarylalkyl group;

n is an integer from 0 to 6;

R is selected from the group consisting of a substituted or unsubstituted $C_1$–$C_{30}$ alkylene group, a substituted or unsubstituted $C_1$–$C_{30}$ alkenylene group, a substituted or unsubstituted $C_1$–$C_{30}$ alkynylene group, a substituted or unsubstituted $C_1$–$C_{30}$ heteroalkylene group, a substituted or unsubstituted $C_6$–$C_{30}$ arylene group, a substituted or unsubstituted $C_7$–$C_{30}$ arylenealkylene group, a substituted or unsubstituted $C_3$–$C_{30}$ heteroarylene group, and a substituted or unsubstituted $C_4$–$C_{30}$ heteroarylenealkylene group;

X is a linker selected from the group consisting of —CONH—, —NHCO—, —COO—, —OCO—, —CO—, —O—, —S—, —SO$_2$—, —SO$_3$—, —O—P(=O)(OH)—O—, and —O—P(OH)—O—; and an aqueous medium.

* * * * *

UNITED STATES PATENT AND TRADEMARK OFFICE
CERTIFICATE OF CORRECTION

| | |
|---|---|
| PATENT NO. | : 7,125,443 B2 |
| APPLICATION NO. | : 10/802949 |
| DATED | : October 24, 2006 |
| INVENTOR(S) | : Kyung-hoon Lee et al. |

Page 1 of 1

It is certified that error appears in the above-identified patent and that said Letters Patent is hereby corrected as shown below:

Column 37, Line 52, change "$C_1 14C_{30}$" to --$C_1$-$C_{30}$--.

Column 39, Line 34, change "heteroalky" to --heteroalkyl--.

Signed and Sealed this

Thirteenth Day of March, 2007

JON W. DUDAS
*Director of the United States Patent and Trademark Office*